United States Patent [19]

Kidwell, Jr.

[11] Patent Number: 4,590,931
[45] Date of Patent: May 27, 1986

[54] SCROTUM PROTECTING GUARD

[75] Inventor: Louis E. Kidwell, Jr., Shreveport, La.

[73] Assignee: Practical Products, Inc., El Paso, Tex.

[21] Appl. No.: 663,956

[22] Filed: Oct. 22, 1984

[51] Int. Cl.⁴ ............................ A61F 5/40; A61F 5/44
[52] U.S. Cl. ..................................... 128/162; 128/158; 128/DIG. 15; 604/347; 604/349
[58] Field of Search ................ 604/347, 349; 128/158, 128/162, DIG. 15

[56] References Cited

U.S. PATENT DOCUMENTS

| | | | |
|---|---|---|---|
| 713,900 | 11/1902 | Miller et al. | |
| 741,173 | 10/1903 | Seidel | |
| 2,138,626 | 6/1938 | Copen | 2/21 |
| 2,222,825 | 11/1940 | Starck | 128/295 |
| 2,864,369 | 4/1956 | Morrow | 128/295 |
| 3,035,579 | 5/1962 | Benovic | 128/295 |
| 3,547,117 | 12/1970 | Smithers | 128/158 |
| 3,707,969 | 1/1973 | Sanford | 128/287 |
| 4,381,782 | 5/1983 | Mazurak | 604/368 |
| 4,453,938 | 6/1984 | Brendling | 604/346 |

Primary Examiner—Herbert S. Cockeram
Attorney, Agent, or Firm—Lowe, King, Price & Becker

[57] ABSTRACT

A scrotum guard for male use comprises substantially identical side walls sealed along edges thereof to establish a sheath formed with an insertion opening. When the guard is in place by inserting the scrotum through the opening, the opening is firmly and gently clamped to grip the genitals by means of hook and loop fastening strips providing an infinitely adjustable fit. A series of elastic gatherers or pleats formed along an edge portion of the opening cooperate with the hook and loop fastening strips to improve retention of the guard in the protective position.

19 Claims, 2 Drawing Figures

SCROTUM PROTECTING GUARD

TECHNICAL FIELD

The present invention generally relates to scrotum protecting guards for male use and, more particularly, to a protective sheath having an adjustable insertion opening.

BACKGROUND ART

Urine collecting incontinence guards are well known for use by males afflicted with poor or no bladder control, particularly when bedridden following surgery or prolonged illness. Generally, the guards of which I am aware are formed as a sheath from moisture impervious material having an inner liquid absorbent layer. A user's penis and often the scrotum is inserted into the sheath which will contain an involuntary discharge of urine.

In various prior art guards of which I am aware, the sheath is usually supported in a protective position on the wearer by a belt encircling the waist and connected to the sheath with a strap, such as disclosed in U.S. Pat. No. 741,173 to Seidel. However, this type of arrangement results in a guard that is complex and bulky in construction and often difficult to attach to bedridden male patients. When worn beneath street clothing, i.e., pants, the use of belts renders the guard uncomfortable to the user.

The insertion opening formed in the prior art sheath discussed supra utilizes a string having ends tied together to clamp the opening to the penis or scrotum to provide further support. However, with this arrangement, a large knot as well as loose ends of the string are disposed outside the sheath which can be noticeable through street clothing due to increased bulkiness if an adult diaper is not worn by the user, as well as uncomfortable to the user.

An incontinence guard disclosed in U.S. Pat. No. 4,453,938 to Brendling is of simpler design than that disclosed in the Seidel patent, and comprises a sheath formed of identical side walls. The side walls are parallelogram shaped and have opposing edges of unequal size and shape establishing an insertion opening wherein these shaped edges are adapted to lie snugly against the base of the penis. However, to retain the guard in protective position, tight fitting retaining pants must be worn which can be uncomfortable for any wearer and is especially impractical for bedridden patients.

It is accordingly an object of the present invention to provide a scrotum protecting guard with an insertion opening having adjustable fastening means permitting both a comfortable and snug fit around the perimeter of the penis or scrotum.

Another object is to provide a guard which can be widely used with different sizes of penis and penis positions that may be encountered.

Still a further object is to provide a guard that is inexpensive to manufacture and can be comfortably worn in a protective position with or without pants.

Yet another object is to provide a guard that can be easily attached and detached from the penis and scrotum.

There exists a need for protecting the scrotum from contact with prepping solutions, as before urology or proctology surgery. Further, it would be desirable to protect the scrotum from contact with fecal matter or urine as likely to occur during adult use of diapers, avoiding expensive nursing personnel time required to clean the patients's scrotum following soiling.

DISCLOSURE OF THE INVENTION

A scrotum protecting guard for male use, in accordance the present invention, comprises a sheath formed of side walls being secured together along edges thereof except for at least one opening formed along one side of said walls and between edges thereof through which the user's scrotum is inserted into the sheath. Means attached to edges of the side walls is provided for clamping the opening to the scrotum or penis to retain the guard in a fixed position. The fastening means preferaby includes a first fastening strip disposed along an edge of the opening and which carries resilient hook fasteners. A second fastening strip disposed along an opposite edge of the opening carries resilient loop fasteners engageable with the hook or mushroom fasteners to provide a snug fit between the opening and periphery of thepenis or scrotum.

The side walls are preferably substantially identical and can be sealed together along their edges with stitching or utilizing heat sealing techniques. Each side wall prefereably has an outer layer of liquid-impermeable or resistant material and a soft inner layer of paper or cloth for comfort and to absorb perspiration. The side walls are easily foldable and sufficiently flexible so that they can be deformed into shape as desired when put into place for comfortable wear by the user.

In accordance with a further aspect of the invention, the first strip of hook or mushroom fasteners is preferably secured flush to an outer surface of one side wall adjacent the opening to extend generally parallel to an edge thereof. The strip of loop fasteners is fastened at one end thereof to an opposite edge of the opening to overlie and contact the hook or mushroom fasteners when the strips are mated together to clamp the guard to the scrotum. The exterior positioning of the hook or mushroom fastening strips prevents contact between the prickly hooks or mushrooms and the user's genitals. The loop fastening strip is preferably of greater length than the hook fastening strip so that a free end of the loop strip may be out of contact with the hook or mushroom strip when said strips are fastened together to establish a release tab manually engageable to permit quick release to the strips from the fastening position for easy removal of the guard. To further assure that contact of the hooks or mushrooms with the user's skin is prevented, the loop strip is preferably of greater width than the hook or mushroom strip. The fastening strips can be either stitched, pressed on by use of pressure sensitive backing, snapped, or taped to the side walls. Snaps or tapes can be used for fastening, as is done in some diapers and hospital garments.

In accordance with a further aspect of the invention, an elastic thread is attached to an edge of the insertion opening to partially surround same and establish a series of permanent gatherers or elastic pleats. These pleats are resiliently yieldable to enable the opening to snugly fasten to the periphery of the scrotum or penis when the fastening strips are secured together. The elastic thread cooperates with the fastening strips to assure that clamping attachment of the insertion opening to the genitals is firm but gentle. The elastic thread is preferably secured to an outer surface of the insertion opening to avoid discomfort due to contact of the thread with the genitals.

Still other objects of the present invention will become readily apparent to those skilled in this art from the following description wherein there is shown and described a preferred embodiment of this invention, simply by way of illustration of one of the best modes contemplated for carrying out the invention. As will be realized, the invention is capable of other different embodiments, and its several details are capable of modifications in various, obvious aspects all without departing from the invention. Accordingly, the drawing and description will be regarded as illustrative in nature and not as restrictive.

BEST MODE FOR CARRYING OUT THE INVENTION

Figure 1:
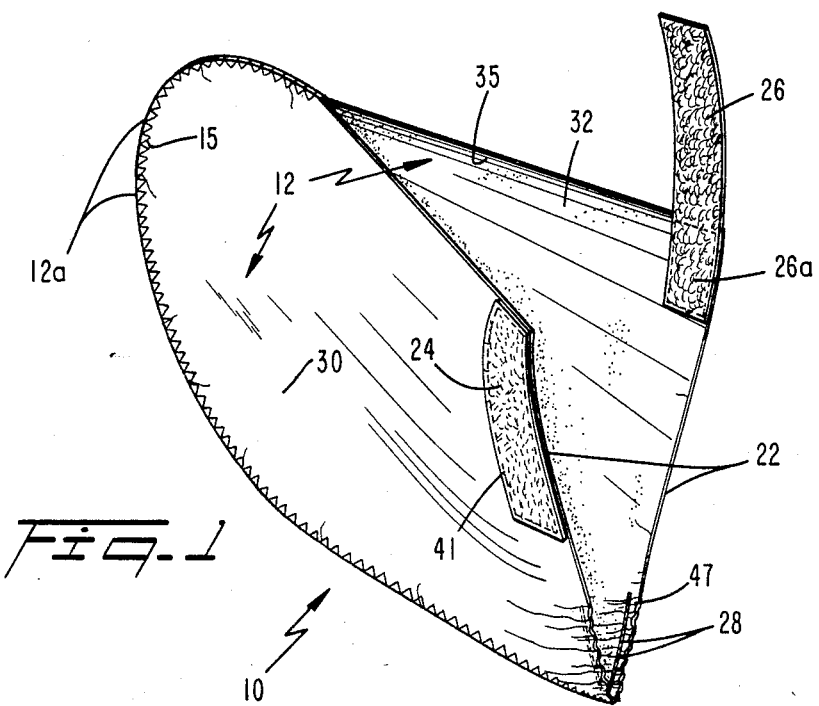
FIG. 1 is a perspective view of an incontinence guard according to the present invention in a partially open position as it is prior to receiving the scrotum of the wearer.
Figure 2:
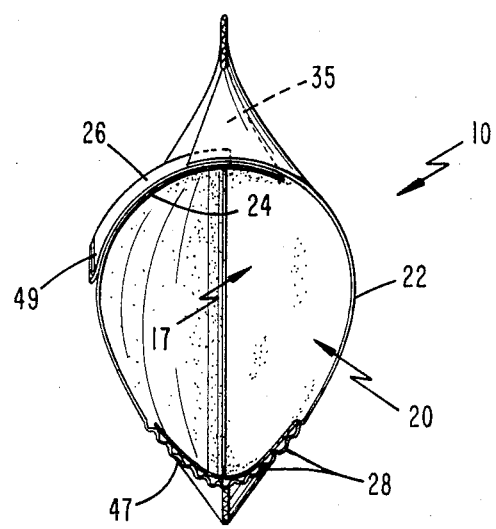
FIG. 2 is a partial perspective, end view of the guard showing the shape of the insertion opening after the fastening strips engage to secure the guard to the penis or scrotum.

Referring to FIGS. 1 and 2, scrotum guard 10 of the present invention comprises a pair of preferably identical side walls 12 stitched or heat sealed together as at 15 to establish a sealed interior cavity 17 into which the male user's scrotum can be received through insertion opening 20. The opening 20, established between edges 22 of side walls 12, is adjustable in size by means of fastening strips 24 and 26 and elastic pleats 28 to gently but firmly grip the periphery of the wearer's scrotum or penis depending on the size of the genitals.

Each side wall 12 is preferably formed with a liquid-impermeable or resistant outer layer 30, such as thin plastic sheeting material, and an inner soft layer 32. The combined layers 30, 32 should be sufficiently flexible and flat so that they are easily foldable and can be deformed into a desired shape for comfort when worn by patients in bed or when put in place and worn beneath a diaper and street clothing. One form of material suitable for use in the present invention is code XXVIII polyethylene blue 65 0.001 inches Taffaflex ® embossed sheeting laminated with Scott Hi-Loft (3030 or 3055), available from Clopay Corporation, Cincinnati, Ohio. The moisture resistant materials such as "Gore-Tex ®", available from W. L. Gore and Assoc., Inc., may also be used, especially for reusable guards.

For ease of manufacture, it is simplest and most economical to fabricate side walls with all side edges thereof straight. However, in accordance with the invention, the forward edge 12 of each side wall is gently curved to semicircular to eliminate sharp corners within the sheath that serve little if any function to achieve more comfort for bed patients and a compact structure that is more comfortable under a diaper when worn with street clothing.

An opening 35 allowing the penis to project upward out of guard 10 is formed adjacent and perpendicular to insertion opening 20 be leaving edges of side walls 12 establishing the opening unattached with respect to each other. However, it will be appreciated that guard 10 can be in place with opening 35 positioned beneath the penis, if the size of the wearer's genitals so warrant.

As shown in FIG. 1, fastening strips 24, 26 are formed from resilient hook and loop strips respectively, such as Aplix fasteners. In a preferred form of attachment, hook strip 24 is secured flush on an outer surface of outer layer 30 of one side wall 12 adjacent opening 20, and extends generally parallel to edge 22. The loop strip 26 is secured at one end 26a thereof to inner layer 32 of the opposite edge 22. The strip 26 projects outward from guard 10 in longitudinal alignment with strip 24 to overlie and contact the hook strip when the strips are mated together to clamp the guard around the scrotum and penis as shown in FIG. 2. One method of attaching tapes 24, 26 to side walls 12 is with stitching 41. Alternatively, heat sealing techniques, pressure sensitive backing on hook and loop strips, snaps or tapes can be utilized to secure the scrotum cover in place such as by encircling strips 24, 26 around the penis (i.e. the hook and loop fasteners can be mated over the penis), or by mating the strips together around the scrotum and beneath the penis. When the fasteners are mated beneath the penis, the penis projects outward over opening 35.

As best shown in FIG. 2, a series of pleats 28 are formed along one end of opening 20 opposite strips 24, 26. Pleats 28 can be formed by means of an elastic thread 47 stitched or otherwise secured to portions of edges 22. Preferably, the thread 47 is stitched to the outer surface of layers 30 to avoid discomfort due to contact of the thread with the genital area. It will be appreciated that pleats 28 are resiliently yieldable and cooperate with fastening tapes 24, 26 to enable opening 20 to be adjustably fitted to the periphery of the base of the penis and/or scrotum to retain guard 10 in protective position in a firm but gentle manner.

It will be appreciated that hook and loop strips 24, 26 can be respectively secured to edges 22 in different configurations to clamp opening 20 to the genitals. However, the hook tape 24 is preferably secured flush to the outside surface of guard 12, as aforesaid, to avoid possible prickly contact with the wearer's skin or genitals. For reliable attachment and to prevent the hooks from rubbing against the wearer's skin, the width of the covering loop tape 26 is preferably greater than hook tape 24. In addition, loop tape 26 is preferably of greater length than hook tape 24 so that under attachment conditions the free end 49 of the loop tape may not contact the hook tape (see FIG. 2) thereby functioning as a quick release tape to permit rapid detachment of guard 10 from the wearer.

In operation, guard 10 protects the scrotum from fecal matter and/or urine, thus minimizing discomfort of the wearer when scrotum must be cleaned and saving expensive nursing personnel time. Guard 10 can also be used to protect the scrotum from contact with prepping solutions before and during surgery and provides support for the scrotum.

The foregoing description of the preferred embodiment of the invention has been presented for purposes of illustration and description. It is not intended to be exhaustive or to limit the invention to the precise form disclosed, and obviously many modifications and variations are possible in light of the above teaching. For example, a strip of mushroom type fastener can be used in place of hook strip 24. Also, as may be seen from FIG. 2, the loop tape may not completely overlie the hook surface, depending on the wearer's needs. Also, it will be obvious in light of the above teaching that guard 10 can be manufactured in reusable form as well as in disposable form. Guard 10 can also be used beneath the diapers of male infants, to protect the scrotum from urine and fecal matter. The embodiment is chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. A scrotum protecting guard for male use, comprising a sheath formed of side walls being secured together along edges thereof except for at least one opening formed along one side of said walls and between edges thereof through which the user's scrotum is inserted into the sheath; and means attached to edges of said side walls for clamping said opening to the genitals to retain the guard in fixed position, said means including a first fastening strip containing resilient hook fasteners disposed along one edge of the opening and a second fastening strip containing resilient loop fasteners disposed along an opposite edge of the opening engageable with the hook fasteners to provide a snug fit.

2. The guard of claim 1, wherein said side walls are sealed together along said edges with stitching.

3. The guard of claim 1, wherein said side walls are sealed together along said edges by heat sealing.

4. The guard of claim 1, further including an elastic thread attached to an edge of said opening to establish a series of gatherers or elastic pleats partially surrounding said opening and being resiliently yieldable to enable said opening to be clamped against the periphery of the scrotum when said fastening strips are secured together.

5. The guard of claim 4, wherein said elastic thread is secured to an inner surface edge of the opening.

6. The guard of claim 4, wherein said elastic thread is secured to an outer surface of said opening to avoid discomfort due to contact of the thread with the genitals.

7. The guard of claim 1, wherein said side walls include a pair of substantially identical side walls.

8. The guard of claim 7, wherein each side wall has an outer layer of liquid impermeable or resistant material and a soft inner layer material.

9. The guard of claim 8, wherein said inner layer is paper or cloth.

10. The guard of claim 1, wherein said strip of hook fasteners is secured flush to an outer surface on one side wall adjacent said opening to extend generally parallel to an edge thereof, and said strip of loop fasteners is fastened at one end thereof to an opposite edge of said opening to overlie and contact the hook fasteners when said strips are mated together to clamp the guard to the genitals.

11. The guard of claim 10, wherein said second fastening strip is of greater length than the first fastening strip so that a free end of said second strip is out of contact with the first strip when said strips are fastened together to thereby establish a release tab manually engageable to permit quick release of said strips from the fastening position.

12. The guard of claim 11, wherein said second strip is of greater width than the first strip.

13. The guard of claim 10, wherein said first and second strips are stitched to said side walls.

14. The guard of claim 10, wherein said first and second strips are attached to said side walls by pressure sensitive backing on hook and loop strips, by strips provided with snap means, or strips provided with tape means.

15. The guard of claim 7, wherein each side wall is formed of two layers of thin, flexible material.

16. The guard of claim 7, further including an opening for receiving the penis formed along an unsealed edge of said side walls extending generally perpendicular to said insertion opening enabling the penis to be positioned outside the guard and allow air to circulate within the guard.

17. A scrotum protecting guard for male use, comprising a sheath formed of a pair of substantially identical side walls being secured together along mating edges thereof except for an opening formed along one side of said walls and between edges thereof through which the user's scrotum is inserted into the sheath; and fastening means attached to said side walls for clamping said opening to the genitals to retain the guard in fixed, snug-fitting position.

18. The guard of claim 1, wherein said mating edges of said side walls formed opposite said opening establish a semicircular forward edge of said guard.

19. A scrotum protecting guard for male use, comprising a sheath formed of side walls being secured together along mating edges thereof except for an opening formed along the top of said walls and along one side of said walls between edges thereof through which the user's scrotum is inserted into the sheath; fastening means attached to edges of said side walls for clamping said opening to the genitals to retain the guard in fixed, snug-fitting position; and a series of elastic pleats formed along an edge portion of said opening opposite the fastening means, said elastic pleats being resiliently yieldable to cooperate with said fastening means so that the opening gently but firmly hugs the periphery of the scrotum or penis when said guard is in place.

* * * * *